(12) United States Patent
Thompson et al.

(10) Patent No.: US 8,557,990 B2
(45) Date of Patent: Oct. 15, 2013

(54) 2,5-DI(METHOXYANILINO) TEREPHTHALIC ACID POLYMORPHS AND QUINACRIDONES REALIZED THEREFROM

(75) Inventors: Brian Thompson, Goose Creek, SC (US); Daphne Rice, Charleston, SC (US); Tracie Tibbs, Charleston, SC (US); Wengan Wu, Mt. Pleasant, SC (US); John Britanak, Summerville, SC (US); Edward H. Sung, Cincinnati, OH (US)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 13/595,994

(22) Filed: Aug. 27, 2012

(65) Prior Publication Data

US 2013/0053568 A1    Feb. 28, 2013

Related U.S. Application Data

(62) Division of application No. 12/301,074, filed as application No. PCT/US2007/011958 on May 21, 2007, now abandoned.

(60) Provisional application No. 60/802,538, filed on May 22, 2006, provisional application No. 60/802,379, filed on May 22, 2006.

(51) Int. Cl.
    *C07D 471/04*    (2006.01)
(52) U.S. Cl.
    USPC .......................................................... 546/49
(58) Field of Classification Search
    USPC .......................................................... 546/49
    See application file for complete search history.

(56) References Cited

U.S. PATENT DOCUMENTS

| | | | |
|---|---|---|---|
| 4,981,997 A | 1/1991 | Schütze et al. | 562/421 |
| 5,236,498 A | 8/1993 | Zaloum et al. | 106/495 |
| 2009/0186200 A1 | 7/2009 | Thompson et al. | 428/195.1 |

FOREIGN PATENT DOCUMENTS

| WO | WO 02/099432 | 12/2002 |
|---|---|---|
| WO | WO 2007/139724 | 12/2007 |

OTHER PUBLICATIONS

Chinese Office Action dated Jun. 25, 2013 for Chinese Patent Application No. 200780018760.3. [11 pages].
International Search Report and Written Opinion, issued Oct. 16, 2007, in connection with corresponding International Patent App. No. PCT/US2007/011958 [9 pages].
International Preliminary Report on Patentability, issued Nov. 27, 2008, in connection with corresponding International Patent App. No. PCT/US2007/011958 [7 pages].
Examination Report, issued Nov. 4, 2009, in connection with corresponding European Patent App. No. 07777168.1 [4 pages].
Office Action, issued Feb. 22, 2012, in connection with corresponding Chinese Patent App. No. 200780018760.3 [9 pages].
Office Action, issued Feb. 27, 2012, in connection with corresponding U.S. Appl. No. 12/301,074 [6 pages].
Examination Report, issued Apr. 11, 2012, in connection with corresponding European Patent App. No. 07777168.1 [4 pages].
Office Action, issued Feb. 17, 2013, in connection with corresponding Chinese Patent App. No. 200780018760.3 [7 pages].
Database CA [online] Chemical Abstracts Service, Columbus, OH, US; Shibata Katsuya et al., "2,5-Diarylaminoterephthalic acids," XP002453496 retrieved from STN Database Accession No. 1976:494083 abstract—JP 51 059830 A (Tekkosha Co., Ltd., Japan) May 25, 1976 [1 page].

*Primary Examiner* — Mark Ruthkosky
*Assistant Examiner* — Ian Rummel
(74) *Attorney, Agent, or Firm* — Frost Brown Todd LLC (57) ABSTRACT

2,5-di(p-methoxyanilino)terephthalic acid crystal types I and II are made by controlling the pH during the recovery of the oxidized product of the condensation of dimethylsuccinyl succinate with p-methoxyaniline. The resulting 2,5-di(p-methoxyanilino)-terephthalic acid can be converted into 2,9-dimethoxyquinacridone or a solid solution thereof having controlled characteristics.

5 Claims, 8 Drawing Sheets

2,5-DI(METHOXYANILINO) TEREPHTHALIC ACID POLYMORPHS AND QUINACRIDONES REALIZED THEREFROM

RELATED APPLICATIONS

This application is a divisional of U.S. patent application Ser. No. 12/301,074, filed Nov. 17, 2008 now abandoned, entitled "2,5-DI(METHOXYANILINO)TEREPHTHALIC ACID POLYMORPHS AND QUINACRIDONES REALIZED THEREFROM," which is the National Stage of International Application Serial No. PCT/US2007/011958, filed May 21, 2007, which claims benefit of priority under 35 U.S.C. §119(e) to U.S. Provisional Patent Application Ser. No. 60/802,538, filed May 22, 2006, entitled "CRYSTAL TYPE I AND II OF 2,5-DI(4-METHOXYANILINO) TEREPHTHALIC ACID," and U.S. Provisional Patent Application Ser. No. 60/802,379, filed May 22, 2006, entitled "2,5-DIMETHOXYQUINACRIDONE AND ITS SOLID SOLUTIONS THEREOF." The disclosure of each of the above-referenced applications is incorporated herein by reference in its entirety.

FIELD OF THE INVENTION

This invention relates to new crystal types of 2,5-di(p-methoxyanilino)-terephthalic acid and their use in the production of 2,9-dimethoxyquinacridone and solid solutions thereof.

BACKGROUND OF INVENTION

A conventional method for the production of pigments which are 2,9-dimethoxyquinacridone or its solid solutions involves the conversion of 2,5-di(p-methoxyanilino)terephthalic acid to the desired quinacridone. Color manipulation of the final pigment can then be achieved by modifying selected post-synthetic quinacridone manufacture treatments so as to cause changes in the particle size, particle shape, particle size distribution and/or crystal form of the final pigment. These steps can entail milling procedures (wet, dry, with and without milling aids) and heat treatments (with and without particle growth inhibitors or dispersing aids). It is also known that the use of fully-formed quinacridone derivatives and/or their quinacridone intermediate precursors during the synthetic ring closure procedure to produce the quinacridone itself can be used as a means to alter the color and physical properties of the quinacridone. To those skilled in the art, the term pigment derivative and derivative precursor is well-known. Such derivatives are usually substituted with either a carbonyl, sulfonyl or other connecting functionality which is reacted with an acid, amine, amide, imide, alkyl or alkoxy-containing moiety.

2,5-di(p-methoxyanilino)terephthalic acid is a well known intermediate used in the production of quinacridones. Conventionally, this intermediate is prepared by reacting dimethylsuccinyl succinate and 4-methoxyaniline in a solvent, such as methanol or a higher alcohol, at elevated temperatures in the presence of an acid, and possibly under pressure. The resulting dicondensed material is combined with an oxidizing agent, such as the sodium salt of m-nitrobenzenesulfonic acid, $H_2O_2$ or air, and a base, such as NaOH or KOH, and subsequently heated to an elevated temperature, possibly under pressure. The resulting 2,5-di(4-methoxyanilino) terephthalic acid or its metal salt is then diluted with water to obtain a solution. A filtering aid, such as Celite, may be added to the solution and insolubles removed. The resulting solution is acidified with an acid, such as HCl or $H_2SO_4$, until the product precipitates.

Polymorphism of the dihydroquinacridone, a quinacridone precursor, and its impact on the resulting quinacridone is well known. Polymorphism exhibited by the quinacridones themselves has also been recognized. For example, P. V. 19's polymorphism is one of the most widely studied and commercialized examples. The polymorphism of other quinacridones, such as for example that of P. R. 122 and P. R. 202, has also been discussed in the literature. However, there is no evidence in the literature that the 2,5-dianilinoterephthalic quinacridone precursors exhibit polymorphism. It has been assumed that these precursors have only one crystal form and that, because the 2,5-dianilinoterephthalic acids supposedly dissolve in the ring closing agent, their physical properties have no impact on the final quinacridone obtained.

It has been discovered that unlike other 2,5-di(anilino) terephthalic acid derivatives, 2,5-di(p-methoxyanilino) terephthalic acid has two distinctly different crystal forms, crystal type I and crystal type II, and that by choosing one of these, the final properties of the quinacridone or solid solution incorporating the 2,9-dimethoxyquinacridone are changed and/or improved.

SUMMARY OF INVENTION

In accordance with the present invention, two distinctly different crystal forms of 2,5-di(p-methoxyanilino)terephthalic acid, crystal type I and crystal type II, are produced by controlling the pH recovery conditions to which the oxidized dicondensed product of dimethylsuccinyl succinate and 4-methoxyaniline is subjected. Crystal type I is characterized by being brown (powder or wet cake) and has the distinctive X-ray pattern shown in FIG. 1 with the strongest peak at about d=6.3 angstroms (2θ=13.9 via CuKα). It can be produced by first adjusting the pH during product recovery to about neutral and thereafter further reducing the pH to about 4.5 to about 6.5. Crystal type II is characterized by being violet (powder or wet cake) and has the distinctive X-ray pattern shown in FIG. 2 with the strongest peak at about d=16.1 angstroms (2θ=5.5 via CuKα). It can be produced by adding a 2,5-di(p-methoxyanilino)terephthalic acid solution to a strong acid such that the final pH is below about 5.0. Alternatively, type I can be converted into type II.

Further in accordance with the present invention, the 2,5-di(p-methoxyanilino)-terephthalic acid is converted into a 2,9-dimethoxyquinacridone or a solid solution thereof whose final properties are changed and/or improved relative to the prior art. The quinacridone intermediate's crystal form during quinacridone production, e.g., ring closure, is employed to manipulate the quinacridone's properties.

The quinacridone can be used as a colorant in inks, coating compositions and masses of materials such as plastics.

DETAILED DESCRIPTION OF INVENTION

The present invention provides two distinctly different crystal forms of 2,5-di(p-methoxyanilino)terephthalic acid—crystal type I and crystal type II. These forms can be differentiated by color (one being brown and one being violet) as well as by X-ray diffraction pattern. It has also been found that substantially pure versions of each form, having a purity of at least about 85%, can be prepared by altering the precipitation method typically used (i.e., adding a solution of 2,5-di(p-methoxyanilino)terephthalic acid to a solution of a strong acid to achieve about pH<5.0 versus adjusting the solution of 2,5-di(p-methoxyanilino)terephthalic acid from a high pH to a pH of about <7.0 with an acid). Hereinafter, the brown crystal form is designated as the crystal type I while the violet crystal form is designated as the crystal type II. Crystal type I is the form previously described in the art.

One way to produce crystal type I or crystal type II of the present invention is to control the pH during the recovery of the oxidized product of the condensation of dimethylsuccinyl succinate and p-anisidine. In the procedure for making the oxidized product, dimethylsuccinyl succinate can be stirred into a liquid such as an alcohol to form a slurry and then combined, under stirring, with p-anisidine. An acid catalyst is added and the mixture is heated to a sufficient temperature and time to accomplish condensation. After cooling to room temperature, an oxidizing agent (such as, but not limited to, m-nitrobenzene sulfonic acid, sodium salt, hydrogen peroxide and/or air) may be added. A base is then added and the mixture heated again to a sufficient temperature and time to accomplish oxidation. Upon cooling to a temperature below the reflux temperature of the solvent, the basic reaction slurry is diluted with water and heated to facilitate solution of the oxidized product in the water, for example to about 60° C.

In order to obtain crystal type I (brown), the solution or slurry pH is first adjusted from its basic pH to about neutral and then further adjusted to about 4.5 to about 6.5. To obtain crystal type II (violet), the solution or slurry is combined with a strong acid such that the resulting pH is below about 5.0. While not being bound by theory, it is believed that the time taken to perform the pH adjustment affects the final crystal type. Crystal type II can also be made by providing a solution of 2,5-di(p-methoxyanilino)terephthalic acid crystal type I having a basic pH and combining said solution with an amount of acid sufficient to make the pH below about 5.0. In all cases, the resulting slurry may be filtered and washed to a conductivity free state with deionized water.

Figure 1:
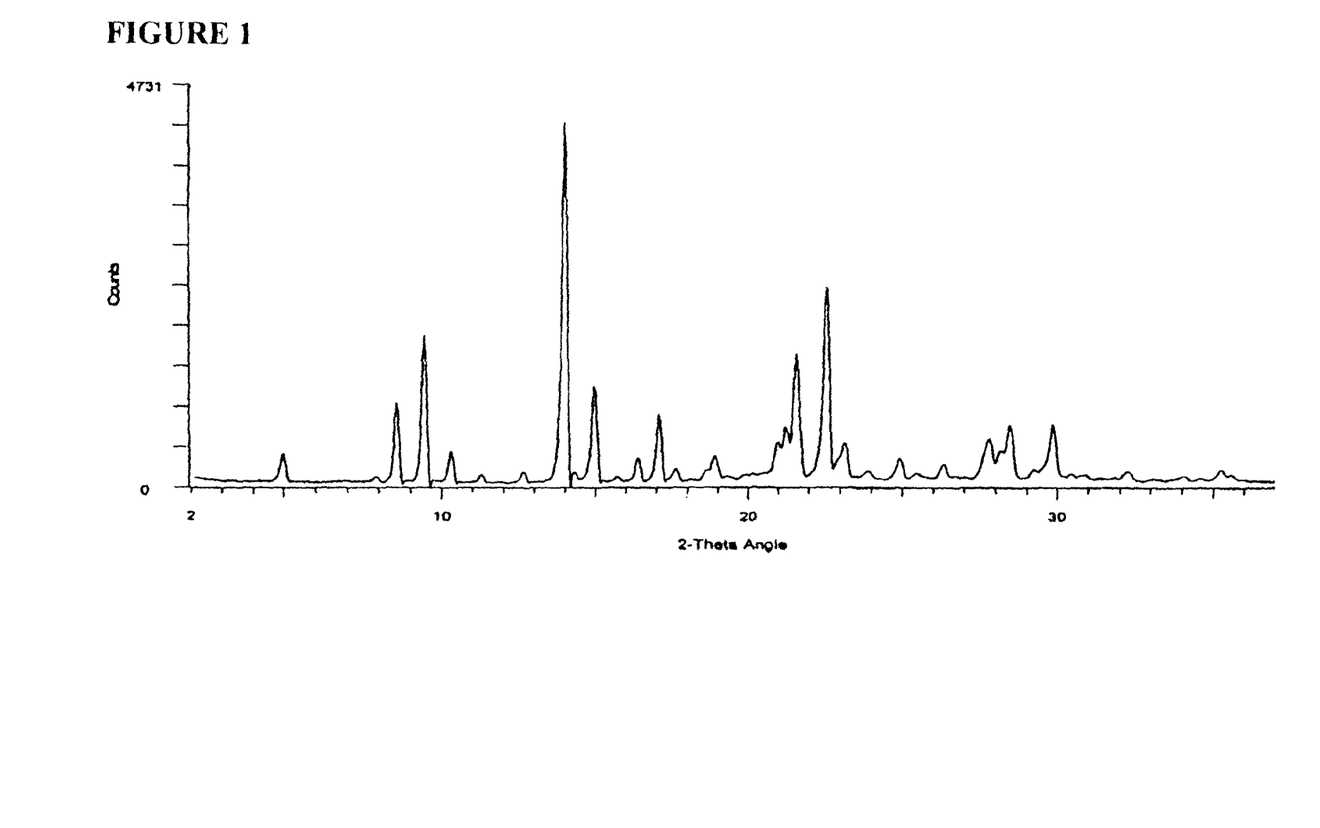
FIG. 1 is the X-ray pattern of 2,5-di(p-methoxyanilino) terephthalic acid crystal type I.
Figure 2:
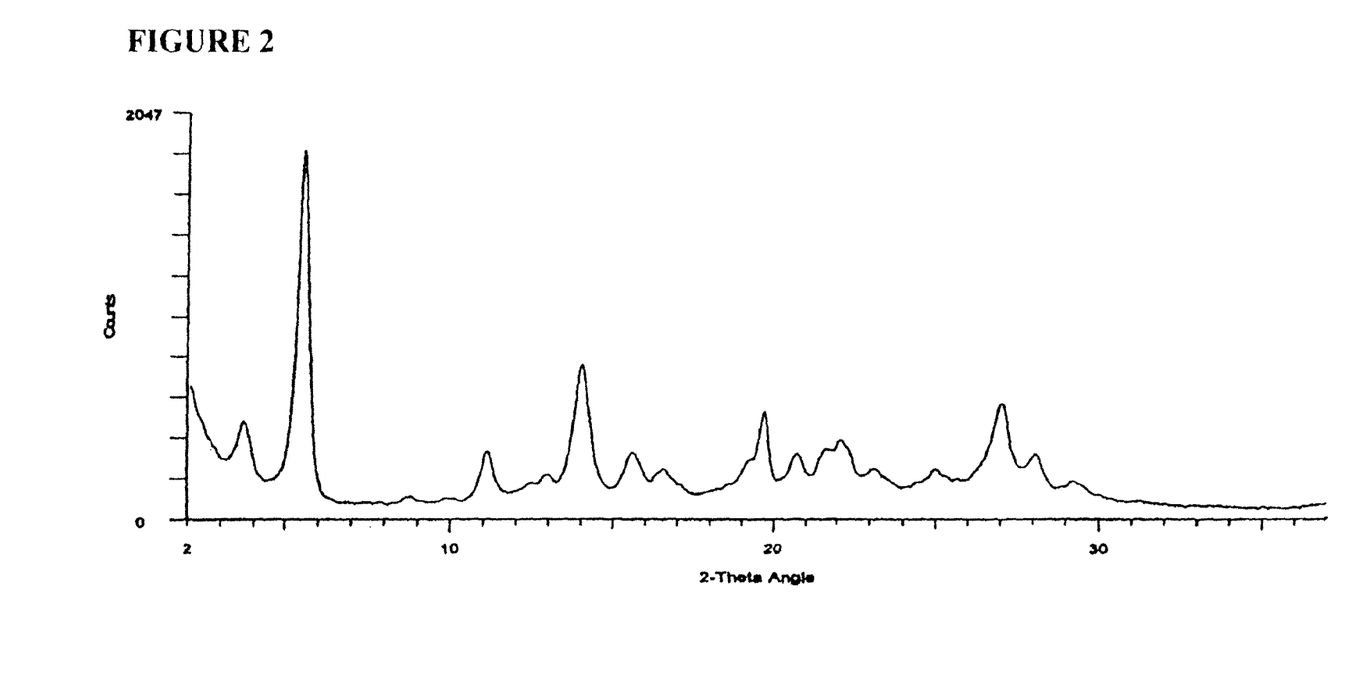
FIG. 2 is the X-ray pattern of 2,5-di(p-methoxyanilino) terephthalic acid crystal type II.

Crystal type I is characterized by being a brown powder or wet cake. The distinctive X-ray pattern of crystal type I is shown in FIG. 1. Crystal type II is characterized by being a violet powder or wet cake, and its distinctive X-ray pattern is shown in FIG. 2.

In the past, crystal morphology of quinacridone pigment precursors has been neglected as a possible way to affect color properties of the final pigment. The current invention, however, allows use of the quinacridone intermediate's crystal form during synthesis (e.g., ring closure) as a method to manipulate the desired quinacridone's color properties. Thus, it has been found that the crystal form of the 2,5-di(p-methoxyanilino)terephthalic acid intermediate used in the synthesis of 2,9-dimethoxyquinacridone and solid solutions thereof, such as, but not limited to, those disclosed in U.S. Pat. No. 5,236,498, has an impact on the coloristic properties of the resulting quinacridone, as shown in Tables 1 and 2 below.

Other solid solutions can be made by ring closing the 2,5-di(p-methoxyanilino)-terephthalic acid with other quinacridone intermediates, such as but not limited to 2,5-di(anilino)terephthalic acid, 2,5-di(toluidino)terephthalic acid and 2,5-di(chloroanilino)-terephthalic acid. Solid solutions can also be made by methods known in the art such as, but not limited to (1) dissolving the crude pigment components in strong mineral acids, such as sulfuric acid, followed by precipitation in a liquid in which they are substantially insoluble, (2) ring closing synthetic intermediates of the quinacridones, before or after oxidation, in strong acids or high boiling solvents, followed by precipitation in a liquid in which they are substantially insoluble, and/or (3) milling the crude quinacridone components together.

The crystal type I and II intermediates can be used in any conventional quinacridone manufacturing process, such as those described in Industrial Organic Pigments by W. Herbst & K. Hunger, published by VCH in 2004, pages 452-472, which is incorporated herein by reference. While both of the type I and type II crystal forms result in a quinacridone that is very attractive with respect to color properties, the different crystal types can be used to impact the resulting quinacridone, which may be the 2,9-dimethoxyquinacridone alone or any solid solution in which it is a part, for example but not limited to those solid solutions disclosed in U.S. Pat. No. 5,236,498 (incorporated herein by reference). It has also been surprisingly found that the crystal type of 2,5-di(p-methoxyanilino)-terephthalic acid can affect the resulting quinacridone coloristically by altering shade hues and chromas. The intermediate's crystal type may also impact the physical properties of the resulting 2,9-dimethoxyquinacridone or its solid solutions in terms of improving surface area, particle size, size distribution, weatherfastness, lightfastness and masstone.

Of course, the crystal form of the intermediate is not the only thing that impacts the color properties of the quinacridone or solid solution. The ring closing conditions chosen may also impact the effect observed on the quinacridone color and physical properties discussed above as they relate to the intermediate's crystal form. In fact, ring closing conditions can be chosen such that the trends observed between the brown and violet crystal forms of 2,5-di(p-methoxyanilino) terephthalic acid can be reversed and/or neutralized, if desired.

The resulting pigment or solid solution pigment of the invention can undergo post treatment by any of the methods known to those skilled in the art to further manipulate and/or improve color, physical and lightfastness properties.

Figure 8:
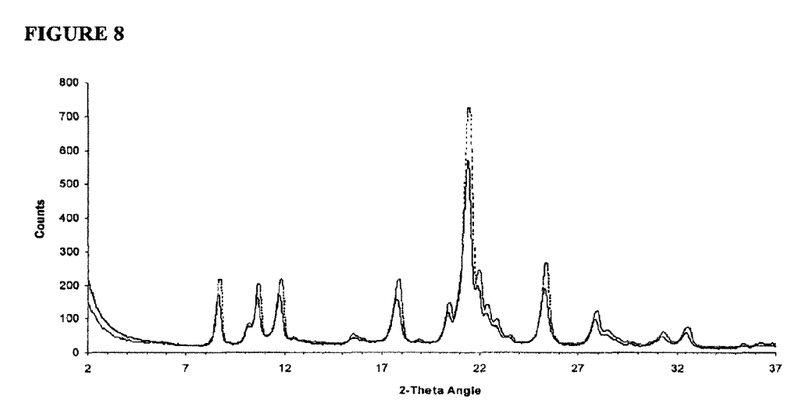
FIG. 8 is X-ray spectra of 2,5-di(anilino)terephthalic acids made by both processes used to obtain 2,5-di(p-methoxyanilino)terephthalic acid crystal types I & II.
Figure 9:
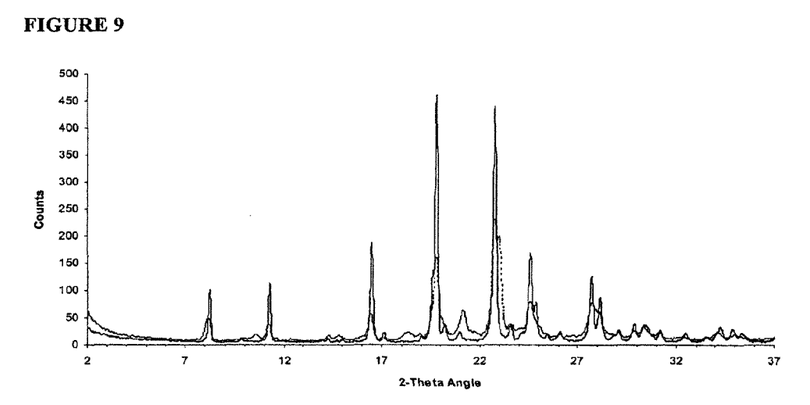
FIG. 9 is X-ray spectra of 2,5-di(4-chloroanilino)terephthalic acids made by both processes used to obtain 2,5-di(p-methoxyanilino)terephthalic acid crystal types I & II.

The invention gives the pigment manufacturer a new and valuable tool to manipulate final pigment properties. Additionally, the knowledge of these two crystal forms and their impact on the final pigment's color properties allows the pigment manufacturer more control over the process. It is always advantageous to produce a known entity in order to control the outcome of subsequent steps. One of the advantages of this invention over prior art is that being able to produce essentially pure versions of each crystal form gives the manufacturer more control over the outcome of the ring closure. Previously, when the 2,5-di(p-methoxyanilino) terephthalic acid was ring closed, no attention was paid to the purity of the crystal form because it was believed that the 2,5-dianilinoterephthalic acids dissolved in the polyphosphoric acid (or other appropriate ring closure or dehydrating agent). The physical properties of the intermediates themselves were also thought to have no impact of relevance on the final product. However, as described above, it has thus been discovered that in fact the 2,5-di(p-methoxyanilino)terephthalic acid is indeed polymorphic, whereas other commonly used quinacridone intermediates such as 2,5-di(aniline)-terephthalic acid (FIG. 8), 2,5-di(toluidino)-terephthalic acid (FIG. 7) and 2,5-di(chloroanilino)-terephthalic acid (FIG. 9) are not polymorphic. Further, it has been found that the polymorphism of the 2,5-di(p-methoxyanilino)terephthalic acid impacts the coloristic properties of the quinacridones and solid solutions in which it is used as the precursor or in combination with other quinacridone precursors.

In order to further illustrate the present invention, various non-limiting examples are set forth below, in which (as throughout this specification and claims) all parts and percentages are by weight and all temperatures in degrees Centigrade, unless otherwise indicated.

EXAMPLES

Example 1

Crystal Type I

Figure 3A:
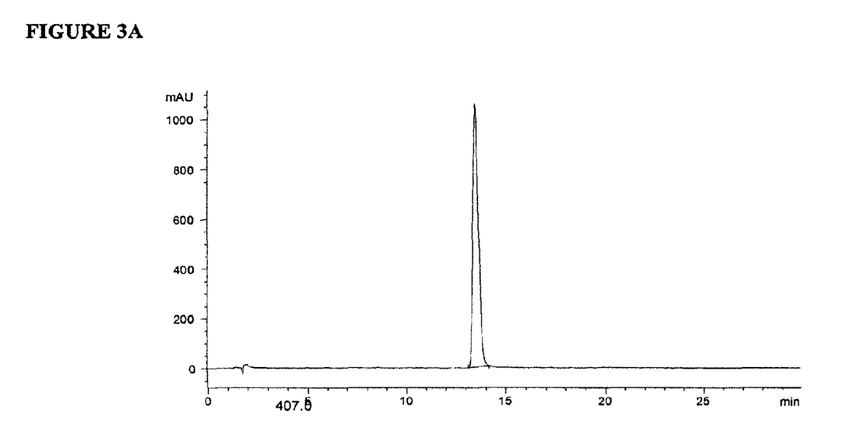
FIGS. 3A to 3C are mass spectra of 2,5-di(p-methoxyanilino)terephthalic acid crystal type I.
Figure 3B:
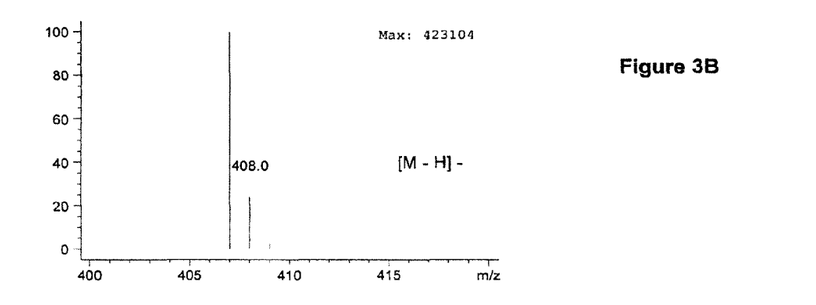
Figure 3C:
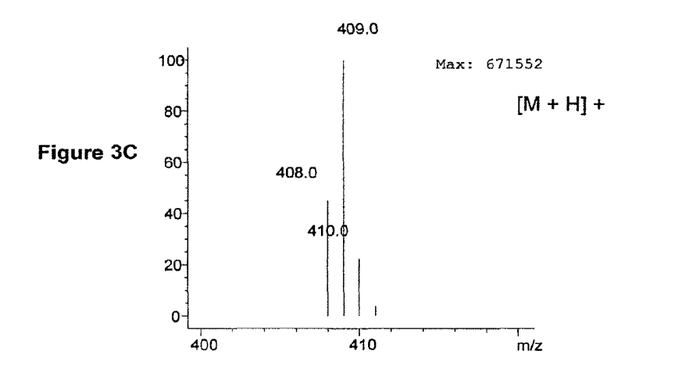

To a pressure reactor were charged 489.8 g of methanol. With agitation, 50 g of dimethylsuccinyl succinate were charged and stirred for ~10 minutes. To the stirring slurry were added 56.7 g of p-anisidine. After stirring for ~15 minutes, 0.8 g of 96% $H_2SO_4$ were added dropwise. The reactor was sealed, heated to 95-100° C. and held at this temperature for approximately 5 hours. After cooling to 40-50° C., the reactor was opened and with agitation, 55.6 g of m-nitrobenzenesulfonic acid, sodium salt, were added. After stirring for ~5 minutes, 127.8 g of 45% KOH were charged over a 15 minute period. The reactor was sealed, heated to 90-95° C. and held at this temperature for approximately 4 hours. Upon cooling to 40-50° C., the reaction slurry was transferred to a container containing 800 g of $H_2O$. Once the transfer was complete, an additional 275 g of $H_2O$ were added and with stirring, the solution was heated to 30-40° C. The pH was then adjusted from 13 to 7.5-7.0 with 40.0 g of 96% $H_2SO_4$. After stirring for 5 minutes, the pH was further adjusted to 5.0-5.5 with 12.8 g of 96% $H_2SO_4$. After stirring for 15 minutes at 30-40° C., the resulting brown slurry was filtered and washed until conductivity free with deionized water. The presscake was dried to obtain approximately 85 g of brown powder. When evaluated by HPLC (Waters system equipped with a 996 PDA detector), the purity was 96.3% 2,5-di(p-methoxyanilino)-terephthalic acid. The sample was also evaluated by LC-MS (Agilent HP1100 LC/MS) to verify the major component as 2,5-di(p-methoxyanilino)terephthalic acid by mass spectrum. The x-ray diffraction of the dry product is shown in FIG. 1 and the mass spectra are shown in FIGS. 3A to 3C.

Elemental analysis of the sample gave the following molecular composition: C=64.77%; H=5.05%; N=6.91%; O=21.94%.

The X-ray data for crystal type I, with very weak diffraction peaks omitted for simplification, are:

| d (in angstroms) | Intensity |
| --- | --- |
| 18.0 | Weak |
| 10.4 | Medium |
| 9.4 | Strong |
| 8.6 | Weak |
| 6.3 | Very strong |
| 5.9 | Medium |
| 5.4 | Weak |
| 5.2 | Medium |
| 4.7 | Weak |
| 4.24 | Weak |
| 4.18 | Medium |
| 3.9 | Strong |
| 3.8 | Weak |
| 3.6 | Weak |
| 3.4 | Weak |
| 3.2 | Weak |
| 3.1 | Medium |
| 3.0 | Medium |

Example 2

Crystal Type II

Figure 4A:
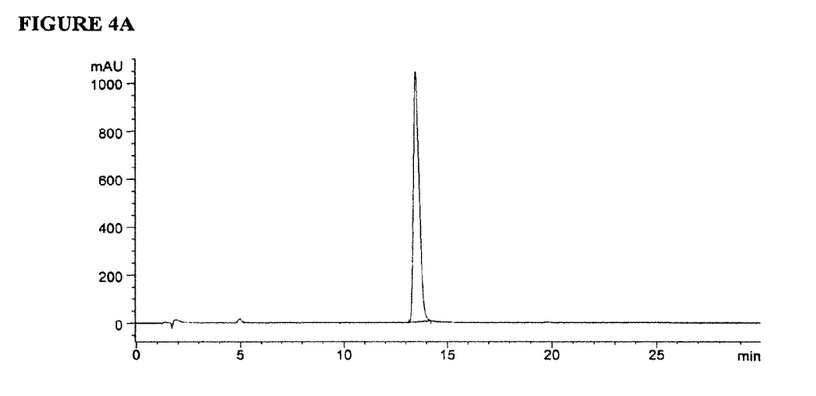
FIGS. 4A to 4C are mass spectra of 2,5-di(p-methoxyanilino)terephthalic acid crystal type II.
Figure 4B:
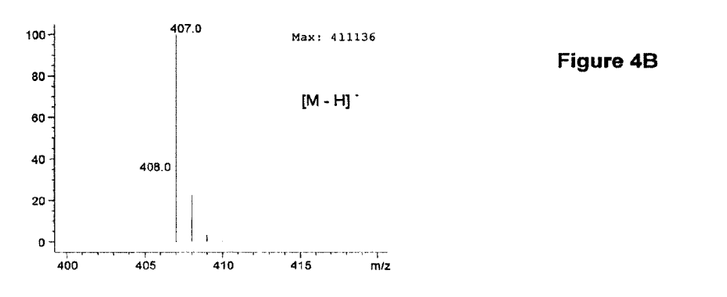
Figure 4C:
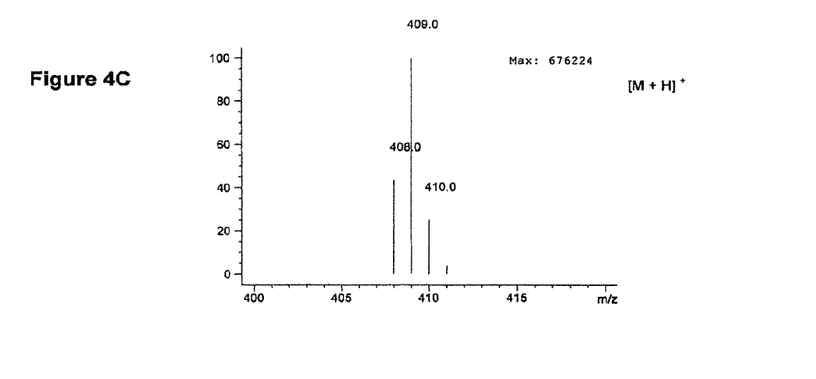

To a pressure reactor were charged 489.8 g of methanol. With agitation, 50 g of dimethylsuccinyl succinate were charged and stirred for ~10 minutes. To the stirring slurry were added 56.7 g of p-anisidine. After stirring for ~15 minutes, 0.8 g of 96% $H_2SO_4$ were added dropwise. The reactor was sealed, heated to 95-100° C. and held at this temperature for approximately 5 hours. After cooling to 40-50° C., the reactor was opened and with agitation, 55.6 g of m-nitrobenzenesulfonic acid, sodium salt, were added. After stirring for ~5 minutes, 127.8 g of 45% KOH were charged over a 15 minute period. The reactor was sealed, heated at 90-95° C. and held at this temperature for approximately 4 hours. Upon cooling to 55-65° C., the reaction slurry was transferred to a container using water to a total volume of 1200 mL. The solution was held 15 minutes at 55-65° C., then transferred over 45-60 minutes, via a pump, to a vessel containing 1344 g of a 3.6% HCl solution. The resulting violet slurry was stirred for 15 minutes at 40-50° C., at which point it had a pH of 1.2. The pH was adjusted with 15 g of 50% NaOH to a pH of 2-2.5. After stirring an additional 20 minutes, the slurry was filtered and the violet presscake was washed conductivity free with water. The presscake was dried to obtain 79.7 g of violet powder. When evaluated by HPLC, the purity was 97% 2,5-di(p-methoxyanilino)terephthalic acid. The x-ray diffraction pattern of the violet product is shown in FIG. 2. The sample was also evaluated by LC-MS to confirm that the major compound was indeed 2,5-di(p-methoxyanilino) terephthalic acid and FIGS. 4A to 4C show the mass spectra. Elemental analysis of the sample gave the following molecular composition: C=64.76%; H=5.10%; N=6.73%; O=22.63%.

The X-ray data for crystal type II, with very weak diffraction peaks omitted for simplification, are:

| d (in angstroms) | Intensity |
|---|---|
| 24.3 | Medium |
| 16.1 | Very strong |
| 8.0 | Medium |
| 6.8 | Weak |
| 6.3 | Strong |
| 5.7 | Medium |
| 5.3 | Weak |
| 4.6 | Weak |
| 4.5 | Medium |
| 4.3 | Medium |
| 4.1 | Medium |
| 4.0 | Medium |
| 3.8 | Weak |
| 3.6 | Weak |
| 3.3 | Medium |
| 3.2 | Medium |

Comparison of the X-ray diffraction pattern (FIG. 2) with the X-ray diffraction pattern of 2,5-di(p-methoxyanilino)terephthalic acid produced by Example 1 (FIG. 1) shows these two are distinct.

Example 3

Figure 5A:
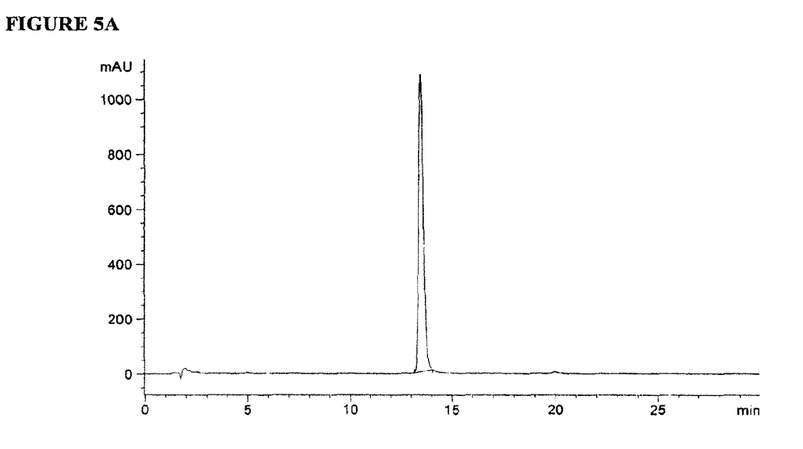
FIGS. 5A to 5C are mass spectra of 2,5-di(p-methoxyanilino)terephthalic acid crystal type II which had been converted from type I.
Figure 5B:
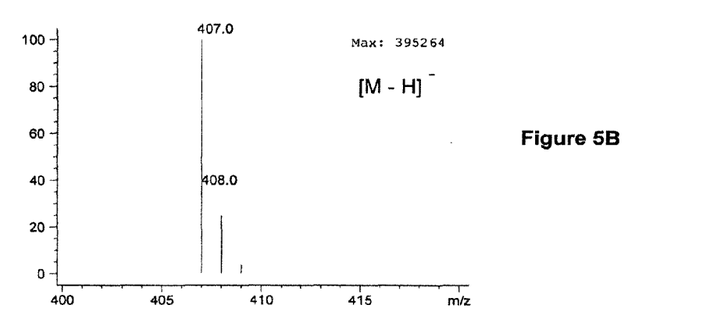
Figure 5C:
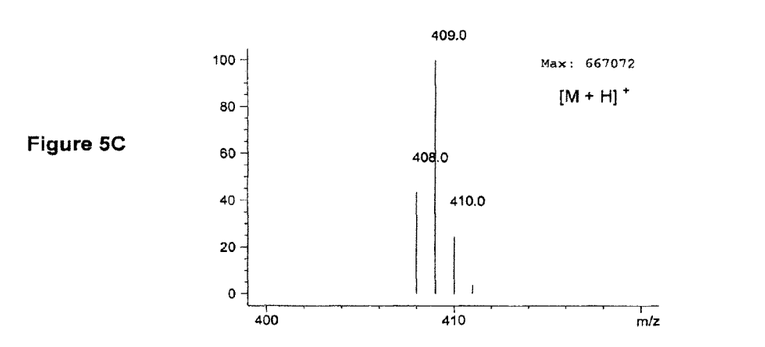
Figure 6:
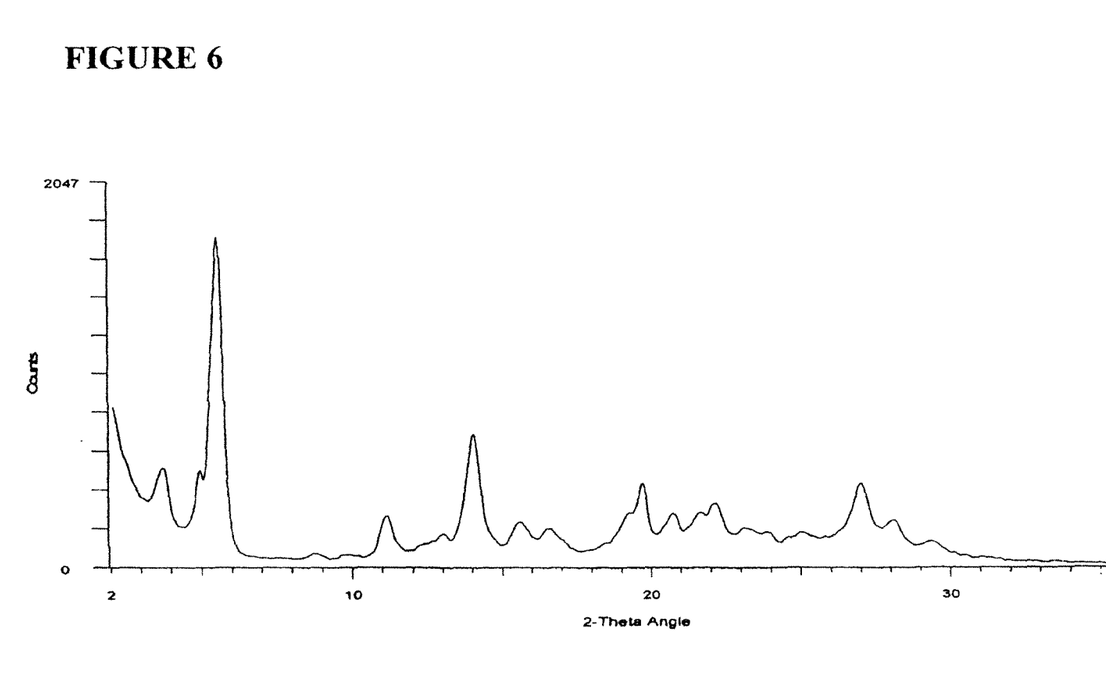
FIG. 6 is an X-ray spectrum of 2,5-di(p-methoxyanilino) terephthalic acid crystal type II which had been converted from type I.

A portion of the brown product of Example 1 (50 g) was dissolved in water having a basic pH (955 g water and 75.2 g 45% KOH). The resulting solution was stirred for 55-65° C. for 60 minutes and then allowed to cool to 35-40° C. The pH was then adjusted from 12.8 to 5.3 with 31.7 g 96% $H_2SO_4$. The resulting violet slurry was stirred for 60 minutes at 35-40° C., at which time it was filtered and the resulting presscake washed with water until conductivity free (<120% of incoming wash water). The washed presscake was then dried in an oven to obtain 43 g of violet powder. When evaluated by HPLC, the purity profile was 93.3% 2,5-di(p-methoxyanilino)terephthalic acid. Evaluation by LC-MS confirmed that the major component was indeed 2,5-di(p-methoxyanilino)terephthalic acid. The mass spectra (FIGS. 5A to 5C) and X-ray diffraction pattern (FIG. 6) confirms that the violet type intermediate was obtained.

Example 4 (Comparative)

To a pressure reactor were charged 300.4 g of methanol, 33.9 g dimethylsuccinyl succinate, 33.9 g of p-toluidine and 0.4 g of 96% $H_2SO_4$. The reactor was sealed and heated to 92-96° C. over approximately 1.5 hours and then held approximately for 5 hours at 92-96° C. After cooling to room temperature, the reactor was opened and 26.2 g of m-nitrobenzenesulfonic acid, sodium salt, were added along with 60.5 g of 50% NaOH and 24 g water. The reactor was sealed and heated at 90-94° C. over 1.5 hours and then held approximately 4 hours at that temperature. Upon cooling to room temperature, the reaction slurry was transferred to a container and the total volume adjusted to 1 liter with water. The resulting slurry was allowed to stir approximately 30 minutes at 35-45° C. The pH was then adjusted from 12 to 5.2 with approximately 96 g of 25% $H_2SO_4$. The resulting violet slurry was allowed to stir for 1 hour at 35-45° C., at which point, it had a pH of 5.5. The slurry was filtered and washed with deionized water to 20 microSiemens. The resulting presscake was dried to obtain approximately 53 g of product which, when evaluated by HPLC, had a purity profile of >90% 2,5-di(p-toluidino)terephthalic acid.

Example 5 (Comparative)

Figure 7:
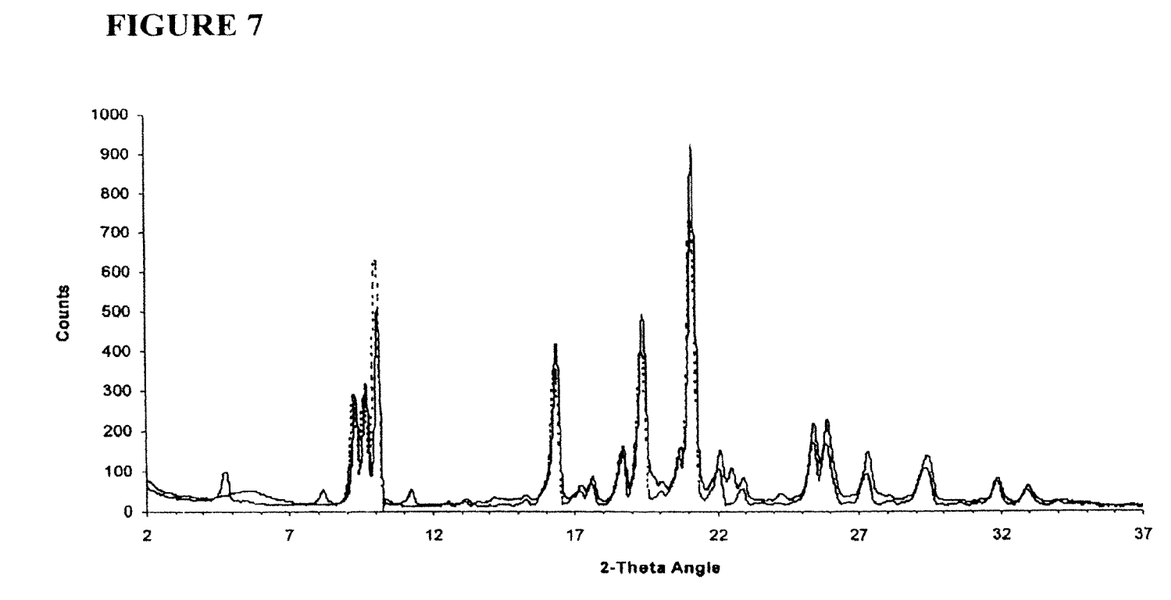
FIG. 7 is X-ray spectra of 2,5-di(p-toluidino)terephthalic acids made by both processes used to obtain 2,5-di(p-methoxyanilino)terephthalic acid crystal types I & II.

To a pressure reactor were charged 300.4 g of methanol, 33.9 g dimethylsuccinyl succinate, 33.9 g of p-toluidine and 0.4 g of 96% $H_2SO_4$. The reactor was sealed and heated to 92-96° C. over approximately 1.5 hours and then held for approximately 5 hours at 92-96° C. After cooling to room temperature, the reactor was opened and 26.2 g of m-nitrobenzenesulfonic acid, sodium salt, were added together with 60.5 g of 50% NaOH and 28 g water. The reactor was sealed and the reaction mixture heated at 90-94° C. over 1.5 hours and then held 4 hours at 90-94° C. Upon cooling to room temperature, the reaction slurry was transferred to a container and the total volume adjusted to 1 liter with water. The solution was held about 30 minutes at 40-50° C. and pH=12. The solution was then transferred, via a pump, to a vessel containing 1008 g of 5.5% $H_2SO_4$ stirring vigorously. The transfer took approximately 1 hour and produced a violet slurry similar to Example 4. The slurry was allowed to stir approximately 1 hour at 40-50° C., pH=1.5. The slurry, having a pH of 1.7, was filtered and washed with deionized water to 18 microSiemens. The resulting presscake was dried to obtain approximately 53 g of product which, when evaluated by HPLC, had a purity profile of >90% 2,5-di(p-toluidino)terephthalic acid. The X-ray diffraction patterns of the products of Example 4 and Example 5 were superimposed, as shown in FIG. 7, and were the same indicating they both had the same crystal form, i.e., there was no polymorphism.

Example 6 (Comparative)

To a pressure reactor were charged 226 g of methanol, 36.0 g dimethylsuccinyl succinate, 35.3 g aniline and 13.2 g glacial acetic acid. The reactor was sealed and heated to 104° C. over approximately 1.5 hours and then held approximately for 5 hours at 104° C. After cooling to room temperature, the reactor was opened and 27 g of m-nitrobenzenesulfonic acid, sodium salt, 74 g of 50% NaOH and 25 g water were added. The reactor was sealed and the reaction heated at 113° C. over 1.5 hours and then held for approximately 4 hours at 113° C. Upon cooling to 63° C., the reaction slurry was transferred to a container and the total volume adjusted to 1 liter with water. The resulting solution was heated to 40° C. and held at 40° C. for 1 hour. The pH was then adjusted from 12.2 to 5.3 with 145.5 g 25% $H_2SO_4$. The resulting violet slurry was allowed to stir 1 hour at 40° C. The pH prior to filtration was 5.4. The slurry was filtered and washed with deionized water to 14 microSiemens. The resulting presscake was dried to obtain approximately 52 g of product. When evaluated by HPLC, the purity profile was >90% 2,5-dianilinoterephthalic acid.

Example 7 (Comparative)

To a pressure reactor were charged 226 g of methanol, 36.0 g dimethylsuccinyl succinate, 35.3 g aniline and 13.2 g glacial acetic acid. The reactor was sealed and heated to 104° C. over approximately 1.5 hours and then held for approximately 5 hours at 104° C. After cooling to room temperature, the reactor was opened and 27 g of m-nitrobenzenesulfonic acid, sodium salt, 74 g of 50% NaOH and 23 g water were added. The reactor was sealed and the reaction heated at 113° C. over 1.5 hours and then held for approximately 4 hours at 113° C. Upon cooling to 53° C., the reaction slurry was transferred to a container and the total volume adjusted to 1 liter to obtain a solution that was held 1 hour at 50° C., pH=12. The solution was then transferred via a pump to a container with 1072 g of 5% H$_2$SO$_4$ stirring vigorously. The transfer took 1 hour, giving a violet slurry similar to Example 6. The slurry was allowed to stir 1 hour at 40° C., pH=2.4. The pH prior to filtration was 2.4. The slurry was filtered and washed with deionized water to 16 microSiemens. The resulting presscake was dried to obtain approximately 51.9 g of product. When evaluated by HPLC, the purity profile was >90% 2,5-dianilinoterephthalic acid. A superimposed X-ray diffraction pattern comparison of the products of Example 7 and Example 6 revealed they had the same crystal form, shown in FIG. 8, i.e., there was no polymorphism. When evaluated by LC-MS, the purity was 95.8% 2,5-dianilinoterephthalic acid.

Example 8 (Comparative)

To a pressure reactor were charged 303 g of methanol, 30.3 g dimethylsuccinyl succinate, 37.9 g 4-chloroaniline and 0.6 g 96% H$_2$SO$_4$. The reactor was sealed and heated to 97° C. over approximately 1.5 hours and then held for approximately 5 hours at 97° C. After cooling to room temperature, the reactor was opened and 33.4 g of m-nitrobenzenesulfonic acid, sodium salt, were added together with 77 g of 50% NaOH and 14 g methanol. The reactor was sealed and the reaction heated at 93° C. over 1.5 hours and then held for approximately 4 hours at 93° C. Upon cooling to 34° C., the reaction slurry was transferred to a container and the total volume adjusted to 1600 mL with water. The resulting solution was heated to 40° C. and the pH was then adjusted from 12.4 to 5.3 with 146.4 g 20% H$_2$SO$_4$ over 1 hour. The resulting red slurry was allowed to stir 1 hour at 40° C. The pH prior to filtration was 5.4. The slurry was filtered and washed with deionized water to 45 microSiemens. The resulting presscake was dried to obtain approximately 52.6 g of product. When evaluated by LC-MS, the purity profile was 95.8% 2,5-di(4-chloroanilino)terephthalic acid.

Example 9 (Comparative)

To a pressure reactor were charged 301.8 g of methanol, 30.0 g dimethylsuccinyl succinate, 37.3 g 4-chloroaniline and 0.6 g 96% H$_2$SO$_4$. The reactor was sealed and heated to 97° C. over approximately 1.5 hours and then held for approximately 5 hours at 97° C. After cooling to room temperature, the reactor was opened and 33.5 g of m-nitrobenzenesulfonic acid, sodium salt, were added together with 77 g of 50% NaOH and 14.8 g methanol. The reactor was sealed and the reaction heated at 93° C. over 1.5 hours and then held approximately 4 hours at 93° C. Upon cooling to room temperature, the reaction slurry was transferred to a container and the total volume adjusted to 1600 mL to obtain a solution that was held 15 minutes at 50° C., pH=11.8. The solution was then transferred via a pump to a container with 806 g of 5.5% H$_2$SO$_4$ stirring vigorously. The transfer took 1.5 hours, giving a violet slurry. The slurry was allowed to stir for 1 hour at 40° C. and a pH of 2. Within 15 minutes, the violet slurry had turned red. The slurry was filtered and washed with deionized water to 16 microSiemens. The resulting presscake was dried to obtain approximately 51.5 g of product. When evaluated by LC-MS, the purity profile was 93.7% 2,5-dianilinoterephthalic acid. A superposed X-ray diffraction pattern comparison of the products of Example 9 and Example 8 (FIG. 9) revealed the same crystal form, i.e., there was no polymorphism.

Example 10

Quinacridone Pigment Solid Solution from Crystal Type I

To a container were charged 360.1 g of 117% polyphosphoric acid and it was then heated to 85° C. with agitation. At 85-95° C., 15.2 g of 2,5-di(4-chloroanilino)terephthalic acid were added over 30-60 minutes. After the 2,5-di(4-chloroanilino)terephthalic acid had dissolved, 45 g of 2,5-di(4-methoxyanilino)terephthalic acid type I prepared according to Example 1 were added over ~90 minutes while maintaining the temperature <115° C. The reaction mixture was allowed to stir 5 hours at 110-115° C. The reaction mixture was then cooled to approximately 90° C. and poured slowly into a container with 900.6 g vigorously stirring methanol over ~15 minutes. The methanol temperature during the drowning step was maintained at <35° C. via an ice-water bath under the container. The violet methanol-pigment slurry was allowed to stir 1 hour at room temperature and then heated to reflux (68-72° C.). The slurry was then held 1 hour at reflux. The slurry was allowed to cool to T<65° C. and then poured into a container containing 1350 g of water. The resulting water/methanol/pigment slurry was held 1 hour at 60° C. and then filtered. The resulting presscake was washed with water to a pH of 3.5. Approximately 135 g presscake at approximately 35.4% solids was obtained, resulting in approximately 48 g solids. From this presscake, approximately 67.8 g presscake (~24 g dry pigment) were reslurried in a quantity of water and methanol sufficient to realize a total of 170 g water and 189 g methanol. The slurry pH was adjusted to approximately 7.3 with dilute NaOH, and then transferred to a Parr pressure reactor and 1.5 g 50% NaOH added. The reactor was sealed and held 6 hours at 120-125° C. After allowing the reaction mixture to cool to room temperature, the slurry was transferred to a beaker. At 40-45° C. and a pH of 11, 2.0 g Dresinate X (manufactured by Hercules) dissolved in water were added to the above stirring slurry. After 30 minutes at 40-45° C., 4 g of calcium chloride dehydrate, dissolved in water, were added to the slurry. After adjusting the total volume to 1 L with water and stirring approximately 15 minutes at 40-45° C., the pH was adjusted to approximately 4.3 with 75% phosphoric acid. After stirring 1 hour at 40-45° C., the slurry was filtered and the resulting presscake washed with water to a conductivity free condition. The presscake was dried to obtain approximately 25.2 g of violet pigment powder and the crystal form was the same as that of the 25% dichloroquinacridone/75% dimethoxyquinacridone reported in U.S. Pat. No. 5,236,498. The color properties of this pigment, when evaluated in a solventborne paint, are shown in Tables 1 and 2.

Example 11

Quinacridone Pigment Solid Solution from Crystal Type II

Three hundred sixty grams of 117% polyphosphoric acid were charged into a container and heated to 85° C. with agitation. At 85-95° C., 15.1 g of 2,5-di(4-chloroanilino)terephthalic acid were added over 30-60 minutes, and after the 2,5-di(4-chloroanilino)terephthalic acid had dissolved, 45 g of 2,5-di(4-methoxyanilino)terephthalic acid type 2 prepared according to Example 2 were added over ~90 minutes while maintaining the temperature <115° C. The reaction mixture was allowed to stir for 5 hours at 110-115° C., then cooled to approximately 90° C. and poured slowly into a container containing 900 g of vigorously stirring methanol over ~15 minutes. The methanol temperature during the drowning was maintained at <35° C. via an ice-water bath under the container. The violet methanol-pigment slurry was allowed to stir 1 hour at room temperature and then heated to reflux (68-72° C.) where the slurry was held for 1 hour. The slurry was allowed to cool to T<65° C. and then poured into a container with 1350 g of water. The resulting water/methanol/pigment slurry was held 1 hour at 60° C. and then filtered. The resulting presscake was washed with water to a pH 3.2. Approximately 274.4 g of presscake were obtained at approximately 19.94% solids, resulting in approximately 54.7 g of solids. From this presscake, 126 g presscake (approximately 25 g dry basis pigment) were reslurried in a quantity of water and methanol sufficient to achieve a total of 150 g water and 150 g methanol. The slurry pH was adjusted to approximately 7.4 with dilute NaOH, and then transferred to a 600-mL Parr pressure reactor and 1.5 g 50% NaOH was added. The reactor was sealed and held 6 h at 120-125° C. After allowing the reaction to cool to room temperature, the slurry was transferred to a 1500 mL beaker. At 40-45° C. and pH of 11.1, 2.0 g Dresinate X dissolved in water were added to the stirring slurry, followed by, after 30 minutes, 4 g of calcium chloride dehydrate, dissolved in water. After adjusting the total volume to 1 L with water and stirring for approximately 15 minutes at 40-45° C., the pH was adjusted to approximately 4.3 with 75% phosphoric acid. After stirring 1 hour at 40-45° C., the slurry was filtered and the resulting presscake washed with water to a conductivity free condition. The presscake was dried to obtain approximately 24 g of violet pigment powder and the crystal form was the same as that of the 25% dichloroquinacridone/75% dimethoxyquinacridone reported in U.S. Pat. No. 5,236,498. The color properties of this pigment, when evaluated in a solventborne paint, are shown in Tables 1 and 2.

Example 12

Paint Evaluation

The pigments of Examples 10 and 11 and a pigment produced according to U.S. Pat. No. 5,236,498 (as a standard) were combined at the same concentration in the same solventborne paint and then evaluated for tint shade and metallic shade. The results relative to the standard are shown in Tables 1 and 2. The data shows that the pigment of Example 10 is distinctly bluer in hue than the pigment produced in Example 11.

TABLE 1

| | | | Tint shade | | | |
|---|---|---|---|---|---|---|
| Pigment | DL | Da | Db | DC | DH | DE |
| Example 10 | 0.22 | −2.19 | 0.49 | −1.62 | −1.55 | 2.26 |
| Example 11 | 0.16 | −1.83 | 1.05 | −1.90 | −0.92 | 2.12 |

TABLE 2

| | | | Metallic shade | | | |
|---|---|---|---|---|---|---|
| Pigment | DL | Da | Db | DC | DH | DE |
| Example 10 | −1.24 | −0.23 | −1.26 | −0.11 | −1.28 | 1.78 |
| Example 11 | −0.61 | −0.59 | −0.13 | −0.58 | −0.17 | 0.86 |

Example 13

Quinacridone Pigment from Crystal Type I

Charged to a container were 360 g of 117% polyphosphoric acid and were heated to 85° C. with agitation. At 85-105° C., 60 g of 2,5-di(4-methoxyanilino) terephthalic acid type I prepared according to Example 1 were added over 60-90 minutes and the reaction mixture was allowed to stir 5 hours at 110-115° C. The reaction mixture was then cooled to approximately 90-95° C. and poured slowly into a container containing 900 g of vigorously stirring methanol over ~15 minutes. The methanol temperature during the drowning was maintained at <35° C. via an ice-water bath under the round bottom flask. The violet methanol-pigment slurry was allowed to stir 1 hour at room temperature and then heated to reflux (68-72° C.) where it was then held for 1 hour. The slurry was allowed to cool to <65° C. and then poured into a container with 1350 g of water. The resulting water/methanol/pigment slurry was held for 3 hours at 60° C. and then filtered. The resulting presscake was washed with water to a pH of 2.9. Approximately 214.3 g presscake were obtained at approximately 26.42% solids, resulting in approximately 56.6 g solids. Approximately 25 g dry basis pigment from the presscake were reslurried in water and methanol to a total of 150 g water and 150 g methanol. The slurry pH was adjusted to approximately 7 with dilute NaOH. The slurry was then transferred to a Parr pressure reactor and 1.5 g 50% NaOH added. The reactor was sealed and held 6 hours at 120-125° C. After allowing the reaction mixture to cool to room temperature, the slurry was transferred to a beaker. At 40-45° C., 2.0 g Dresinate X dissolved in water were added to the stirring slurry. After 30 minutes at 40-45° C., 4 g of calcium chloride dehydrate, dissolved in water, were added to the slurry. After adjusting the total volume to 1 L with water and stirring for approximately 15 minutes at 40-45° C., the pH was adjusted to 4-4.5 with 75% phosphoric acid. After stirring 1 hour at 40-45° C., the slurry was filtered and the resulting presscake washed with water to conductivity free. The presscake was dried to obtain approximately 24 g of violet pigment powder.

Example 14

Quinacridone Pigment from Crystal Type II

Three hundred sixty grams of 117% polyphosphoric acid were placed in a container and heated to 85° C. with agitation. At 85-107° C., 60 g of 2,5-di(4-methoxyanilino)terephthalic acid type II prepared according to Example 2 were added over 60-90 minutes, and the reaction mixture allowed to stir for 5 hours at 110-115° C. The reaction mixture was then cooled to approximately 90-95° C. and poured slowly into a container which contained 900 g vigorously stirring methanol over ~15 minutes. The methanol temperature during the drowning was maintained at <35° C. via an ice-water bath under the container. The violet methanol-pigment slurry was allowed to stir 1 hour at room temperature and then heated to reflux (68-72° C.) where it was held 1 hour, followed by being allowed to cool to T<65° C. and then poured into a container with 1350 g of water. The resulting water/methanol/pigment slurry was held 3 hours at 60° C. and then filtered. The resulting presscake was washed with water to a pH of 2.9. Approximately 128.3 g presscake was obtained at approximately 45.75% solids, resulting in approximately 58.7 g solids being obtained. Approximately 25 g dry basis pigment from the presscake were reslurried in water and methanol to a total of 150 g water and 150 g methanol, and the slurry pH was adjusted to approximately 7 with dilute NaOH. The slurry was then transferred to a Parr pressure reactor and 1.5 g 50% NaOH added. The reactor was sealed and held for 6 h at 120-125° C. After allowing the reaction to cool to room temperature, the slurry was transferred to another container. At 40-45° C., 2.0 g Dresinate X dissolved in water were added to the stirring slurry. After 30 minutes at 40-45° C., 4 g of calcium chloride, dissolved in water, were added to the slurry, and after adjusting the total volume to 1 L with water and stirring for approximately 15 minutes at 40-45° C., the pH was adjusted to 4-4.5 with 75% phosphoric acid. After stirring 1 hour at 40-45° C., the slurry was filtered and the resulting presscake washed with water to a conductivity free condition. The presscake was dried to obtain approximately 24 g of violet pigment powder.

Various changes and modifications can be made to the preferred embodiments described above without departing from the spirit and scope of the invention. The embodiments set forth were intended to be illustrative only and were not intended to limit the invention.

The invention claimed is:

1. A method for preparing 2,5-di(p-methoxyanilino)terephthalic acid crystal type II, comprising:
    dissolving 2,5-di(p-methoxyanilino)terephthalic acid crystal type I in a solvent with a basic pH; and
    precipitating 2,5-di(p-methoxyanilino)terephthalic acid crystal type II by adjusting the pH of the solvent to about 5.5 or lower, wherein:
    crystal type I is brown and has an x-ray diffraction pattern that exhibits the strongest peak at d=6.3 angstroms (2θ=13.9 via CuKα); and
    crystal type II is violet and has an x-ray diffraction pattern that exhibits the strongest peak at d=16.1 angstroms (2θ=5.5 via CuKα).

2. The method of claim 1, wherein the basic pH is a pH of about 12.8 or higher.

3. The method of claim 1, further comprising converting the 2,5-di(p-methoxyanilino)terephthalic acid crystal type II to 2,9-dimethoxyquinacridone.

4. The method of claim 3, wherein the converting comprises ring closure of the 2,5-di(p-methoxyanilino)terephthalic acid crystal type II.

5. A method for making an ink, coating composition, or pigmented article comprising making 2,9-dimethoxyquinacridone by the process of claim 3; and
    forming an ink, coating composition, or pigmented article from the 2,9-dimethoxyquinacridone.

* * * * *